US 9,782,580 B2

(12) United States Patent
Pianca et al.

(10) Patent No.: US 9,782,580 B2
(45) Date of Patent: Oct. 10, 2017

(54) PERCUTANEOUSLY IMPLANTABLE PADDLE-TYPE LEAD AND METHODS AND DEVICES FOR DEPLOYMENT

(71) Applicant: BOSTON SCIENTIFIC NEUROMODULATION CORPORATION, Valencia, CA (US)

(72) Inventors: Anne Margaret Pianca, Santa Monica, CA (US); Douglas Michael Ackermann, Palo Alto, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/048,725

(22) Filed: Feb. 19, 2016

(65) Prior Publication Data

US 2016/0166829 A1 Jun. 16, 2016

Related U.S. Application Data

(62) Division of application No. 13/299,725, filed on Nov. 18, 2011, now Pat. No. 9,265,934.

(60) Provisional application No. 61/419,372, filed on Dec. 3, 2010.

(51) Int. Cl.
*A61N 1/05* (2006.01)

(52) U.S. Cl.
CPC ......... *A61N 1/0553* (2013.01); *A61N 1/0558* (2013.01)

(58) Field of Classification Search
CPC ...... A61N 1/05; A61N 1/0553; A61N 1/0587; A61N 1/0592; A61B 5/2005

USPC ................................. 607/116, 117, 152, 142
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,587,733 B1 | 7/2003 | Cross, Jr. et al. | |
| 6,609,029 B1 | 8/2003 | Mann et al. | |
| 6,609,032 B1 | 8/2003 | Woods et al. | |

(Continued)

OTHER PUBLICATIONS

Official Communication for U.S. Appl. No. 13/299,725 dated Jan. 14, 2015.

(Continued)

*Primary Examiner* — Christopher D Koharski
*Assistant Examiner* — Roland Dinga
(74) *Attorney, Agent, or Firm* — Lowe Graham Jones PLLC; Bruce E. Black

(57) ABSTRACT

A percutaneously implantable paddle lead includes an elongated lead body having a proximal portion and a distal portion; a plurality of terminals disposed on the proximal portion of the lead; a flexible paddle body coupled to the distal portion of the lead; and a plurality of electrodes disposed in the paddle body and electrically coupled to the terminals on the proximal portion of the lead. The percutaneously implantable paddle lead also includes a bonding material in contact with the paddle body and holding the paddle body in a compacted form prior to, and during, insertion into a percutaneous implantation tool. The bonding material is configured and arranged to release the paddle body during or soon after implantation into a patient so that the paddle body can deploy into its paddle-like form. Alternatively, at least one current-degradable fastener can be used instead of the binding material.

19 Claims, 9 Drawing Sheets

(56) References Cited

U.S. PATENT DOCUMENTS

| | | |
|---|---|---|
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,244,374 B1 * | 8/2012 | Swanson .............. A61N 1/0553 607/117 |
| 9,265,934 B2 * | 2/2016 | Pianca ................ A61N 1/0558 |
| 2005/0165465 A1 | 7/2005 | Pianca et al. |
| 2005/0209653 A1 | 9/2005 | Herbert et al. |
| 2007/0150036 A1 | 6/2007 | Anderson |
| 2007/0191709 A1 | 8/2007 | Swanson |
| 2007/0219595 A1 | 9/2007 | He |
| 2008/0071320 A1 | 3/2008 | Brase |

OTHER PUBLICATIONS

Official Communication for U.S. Appl. No. 13/299,725 dated Jun. 10, 2015.

\* cited by examiner

PERCUTANEOUSLY IMPLANTABLE PADDLE-TYPE LEAD AND METHODS AND DEVICES FOR DEPLOYMENT

CROSS-REFERENCE TO RELATED APPLICATIONS

This application is a divisional of U.S. patent application Ser. No. 13/299,725 filed Nov. 18, 2011, which issued as U.S. Pat. No. 9,265,934 on Feb. 23, 2016, which claims the benefit under 35 U.S.C. §119(e) of U.S. Provisional Patent Application Ser. No. 61/419,372 filed on Dec. 3, 2010, both of which are incorporated herein by reference.

FIELD

The present invention is directed to the area of devices and methods for stimulation of tissue using an array of electrode contacts, as well as methods of making and using the devices. In addition, the present invention is directed to the area of devices and methods for stimulation of tissue using a percutaneously deliverable paddle lead.

BACKGROUND

Stimulation systems have been developed to provide therapy for a variety of disorders, as well as for other treatments. For example, stimulation systems can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc. Spinal cord stimulation is a well accepted clinical method for reducing pain in certain populations of patients.

Implantable stimulation devices have been developed to provide therapy for a variety of treatments. For example, implantable stimulation devices can be used to stimulate nerves, such as the spinal cord, muscles, or other tissue. An implantable stimulation device typically includes an implanted control module (with a pulse generator), a lead, and an array of stimulator electrode contacts. The stimulator electrode contacts are implanted in contact with or near the nerves, muscles, or other tissue to be stimulated. The pulse generator in the control module generates electrical pulses that are delivered by the electrode contacts to body tissue. As an example, electrical pulses can be provided to the dorsal column fibers within the spinal cord to provide spinal cord stimulation.

The stimulation electrode contacts may be disposed on a percutaneous spinal cord stimulation lead or a paddle-type lead. Percutaneous spinal cord stimulation leads are at risk of migration once implanted. As a result of lead migration, electrode contacts may be in a nontherapeutic location or may have a suboptimal orientation relative to another implanted lead. In contrast, paddle-type leads mitigate these problems associated with percutaneous leads due to their larger relative size and fixed electrode orientation. Unfortunately, their size requires a more invasive surgical implantation procedure than that used for percutaneous leads. Thus, implantation of conventional paddle-type leads may include invasive procedures such as a laminotomy or laminectomy. This invasive surgery typically requires surgical training and can be time consuming and costly.

BRIEF SUMMARY

One embodiment is a percutaneously implantable paddle lead that includes an elongated lead body having a proximal portion and a distal portion; a plurality of terminals disposed on the proximal portion of the lead; a flexible paddle body coupled to the distal portion of the lead; and a plurality of electrodes disposed in the paddle body and electrically coupled to the terminals on the proximal portion of the lead. The percutaneously implantable paddle lead also includes a bonding material in contact with the paddle body and holding the paddle body in a compacted form prior to, and during, insertion into a percutaneous implantation tool. The bonding material is configured and arranged to release the paddle body during or soon after implantation into a patient so that the paddle body can deploy into its paddle-like form.

Another embodiment is a percutaneously implantable paddle lead that includes an elongated lead body having a proximal portion and a distal portion; a plurality of terminals disposed on the proximal portion of the lead; a flexible paddle body coupled to the distal portion of the lead; and a plurality of electrodes disposed in the paddle body and electrically coupled to the terminals on the proximal portion of the lead. The percutaneously implantable paddle lead further includes at least one current-degradable fastener in contact with the paddle body and holding the paddle body in a compacted form prior to, and during, insertion into a percutaneous implantation tool. The current-degradable fastener is configured and arranged to release the paddle body upon application of at least a threshold current to allow the paddle body to deploy into its paddle-like form.

Yet another embodiment is a method of percutaneously implanting an implantable paddle lead. The method includes inserting at least a paddle body of the paddle lead into a percutaneous insertion tool. The paddle body is compacted into a form that is percutaneously implantable and includes a degradable binding material in contact with the paddle body and holding the paddle body in its compacted form. The method further includes implanting the paddle body near tissue to be stimulated in a body of a patient; and degrading the binding material to release the paddle body from its compacted form and allow it to deploy to its paddle-like form.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

Figure 2A:
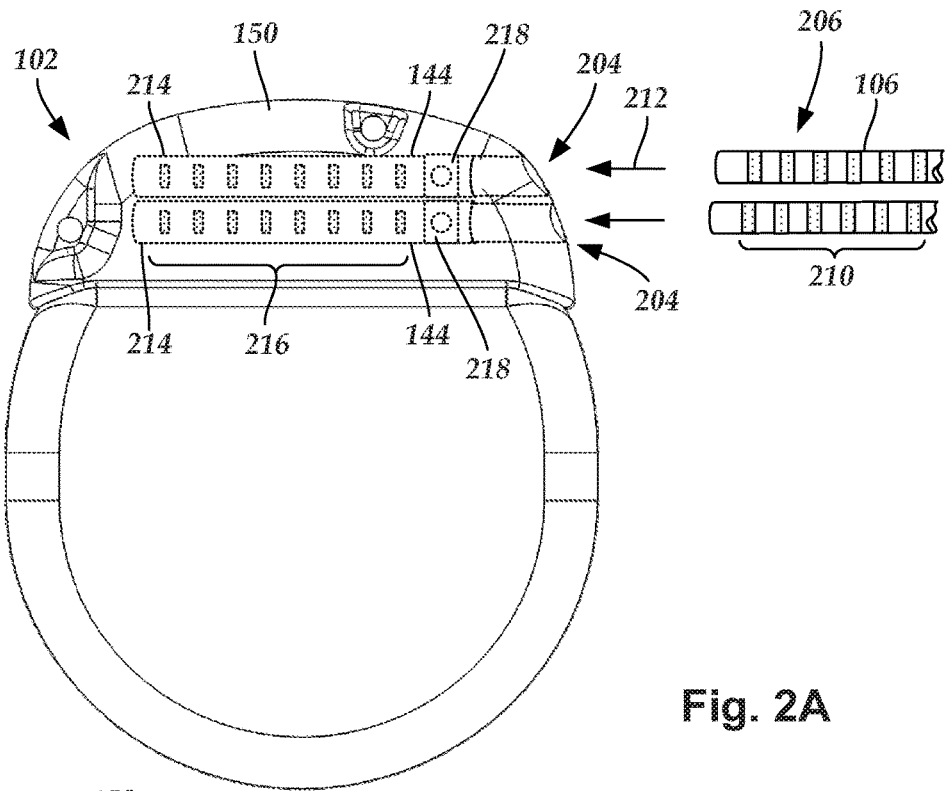
FIG. 2A is a schematic side view of one embodiment of a plurality of connector assemblies disposed in the control module of FIG. 1, the connector assemblies configured and arranged to receive the proximal portions of the lead bodies of FIG. 1, according to the invention.
Figure 2C:
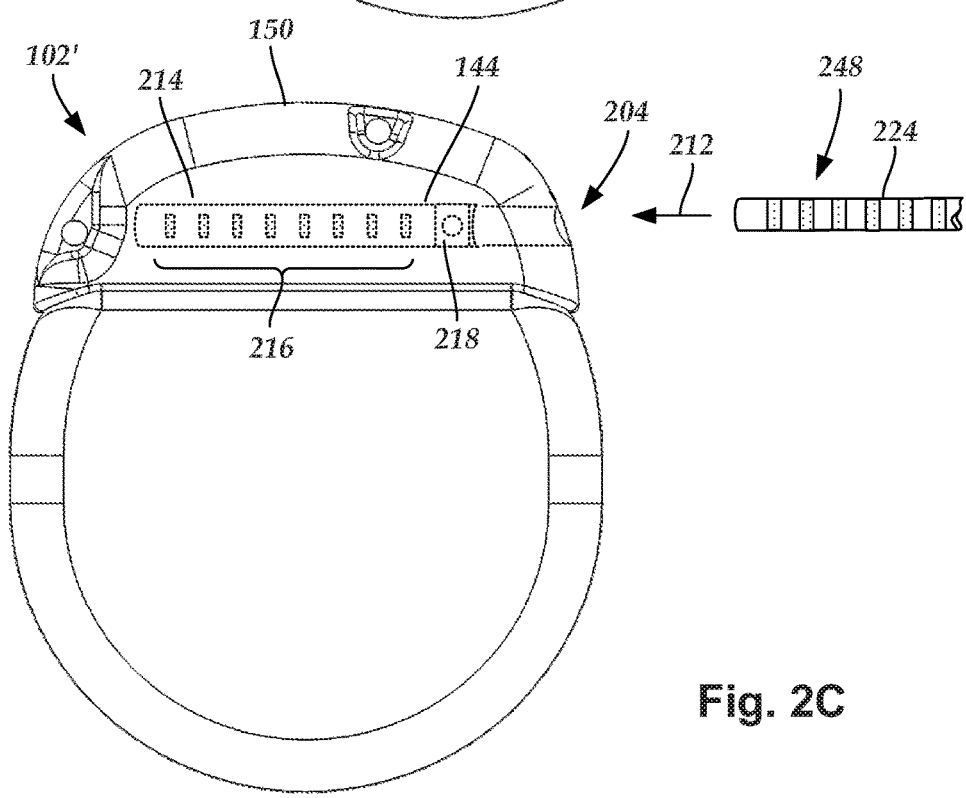
FIG. 2C is a schematic side view of one embodiment of a connector assembly disposed in the control module of FIG.
Figure 2B:
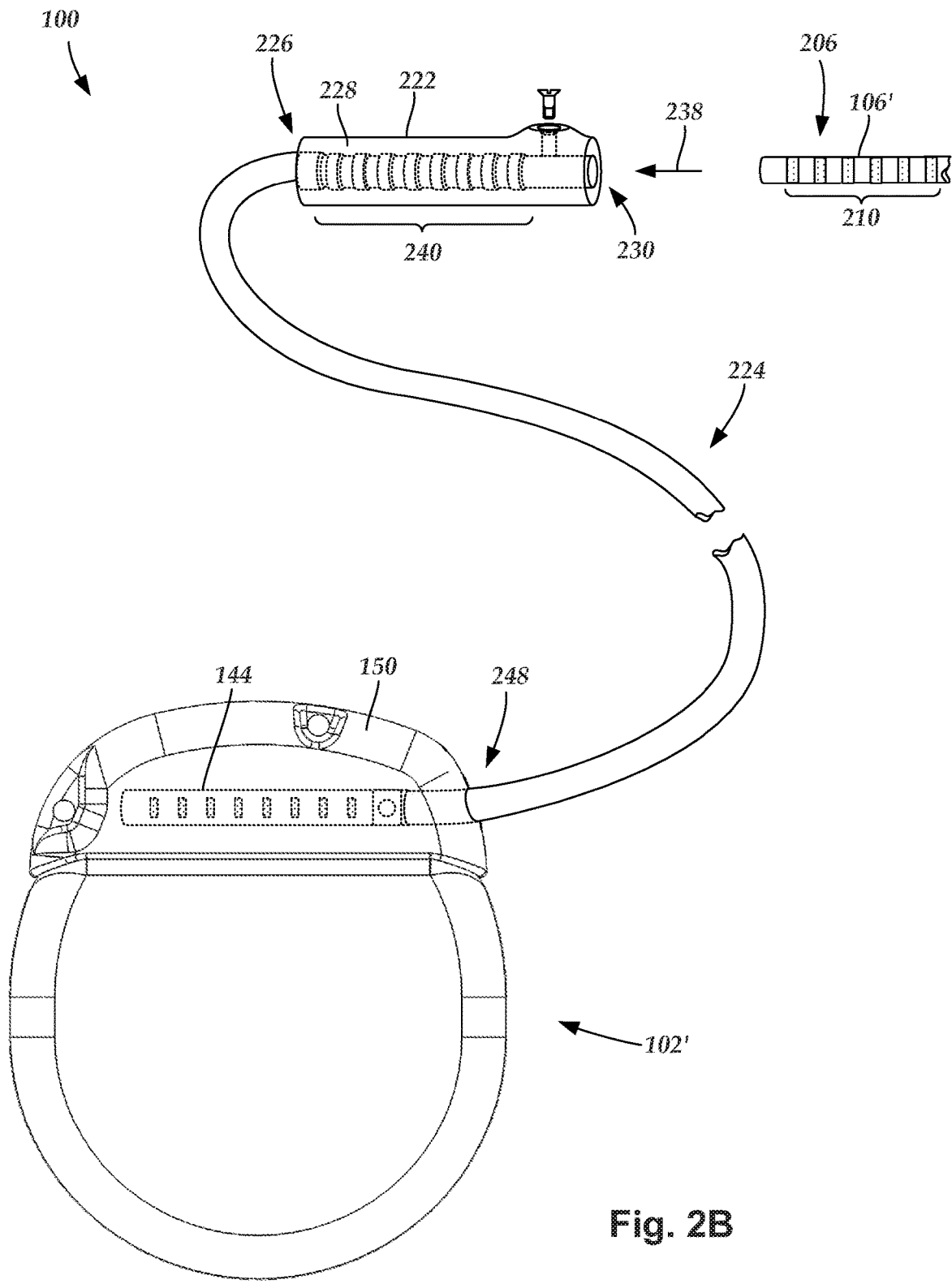
FIG. 2B is a schematic side view of one embodiment of a proximal portion of a lead body and a lead extension coupled to a control module, the lead extension configured and arranged to couple the proximal portion of the lead body to the control module, according to the invention.
Figure 3A:
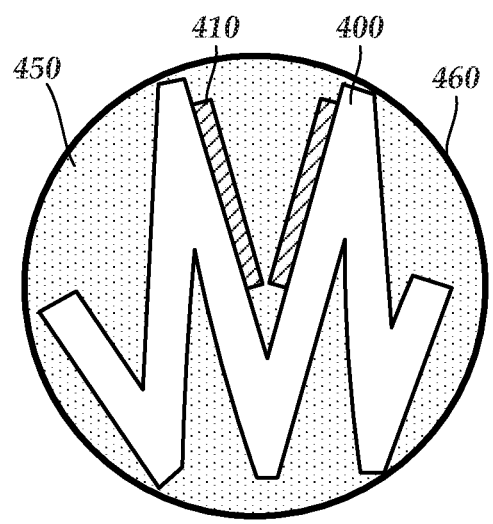
Figure 3B:
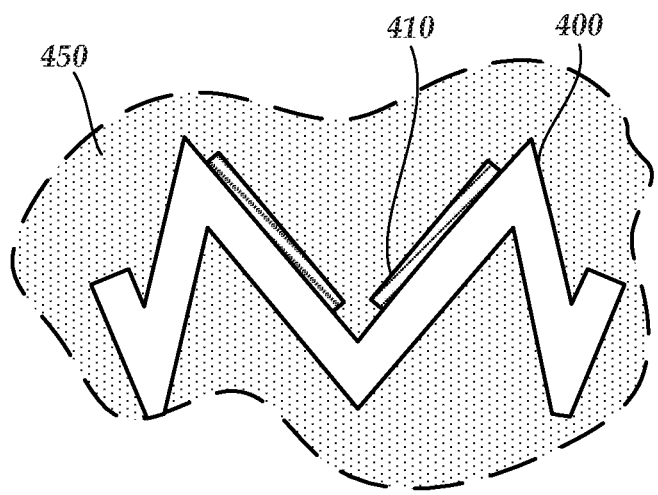
Figure 3C:
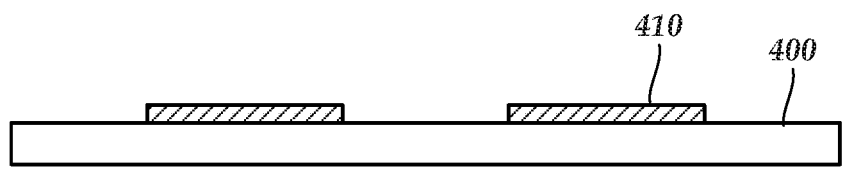
Figure 4A:
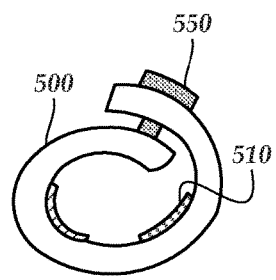
Figure 4B:
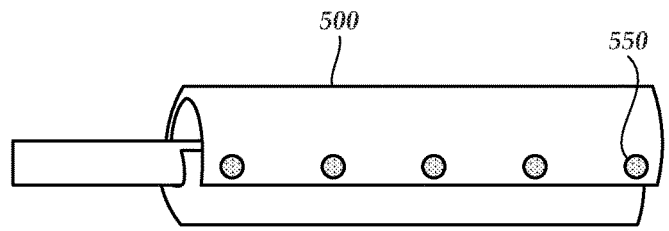
Figure 4C:
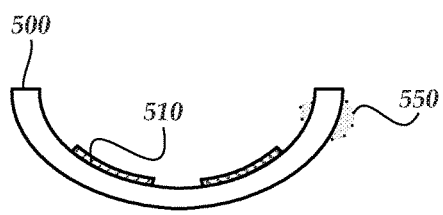
Figure 4D:
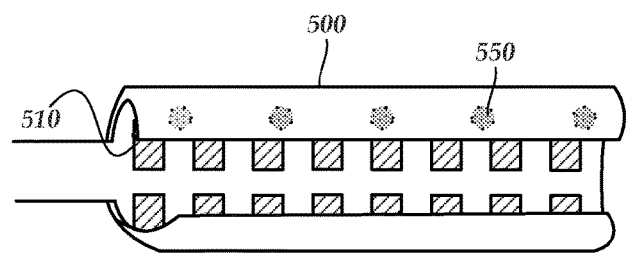
Figure 4E:
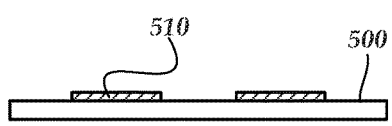
Figure 4F:
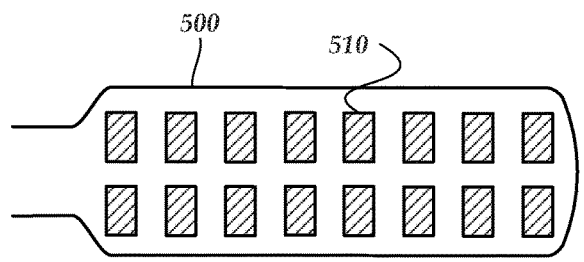
Figure 5A:
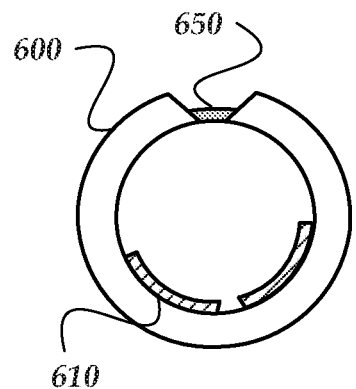
Figure 5B:
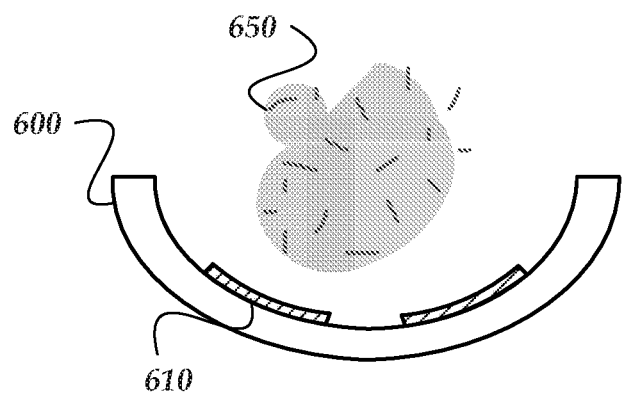
Figure 5C:
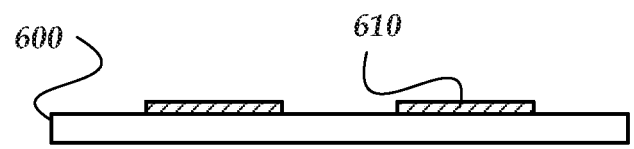
Figure 6A:
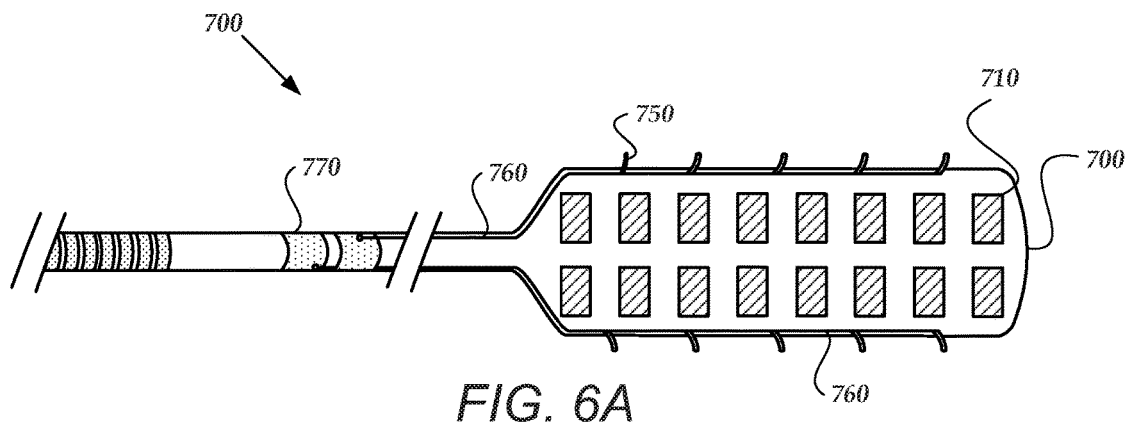
Figure 6B:
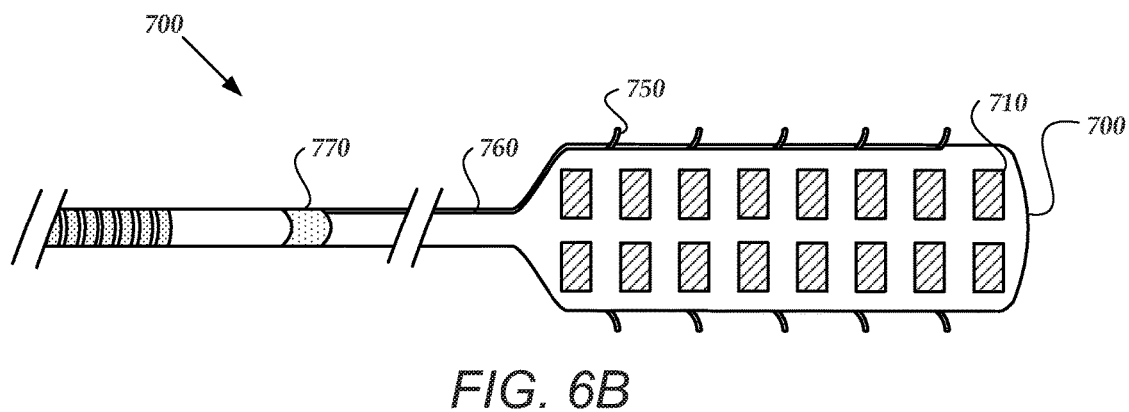
Figure 6C:
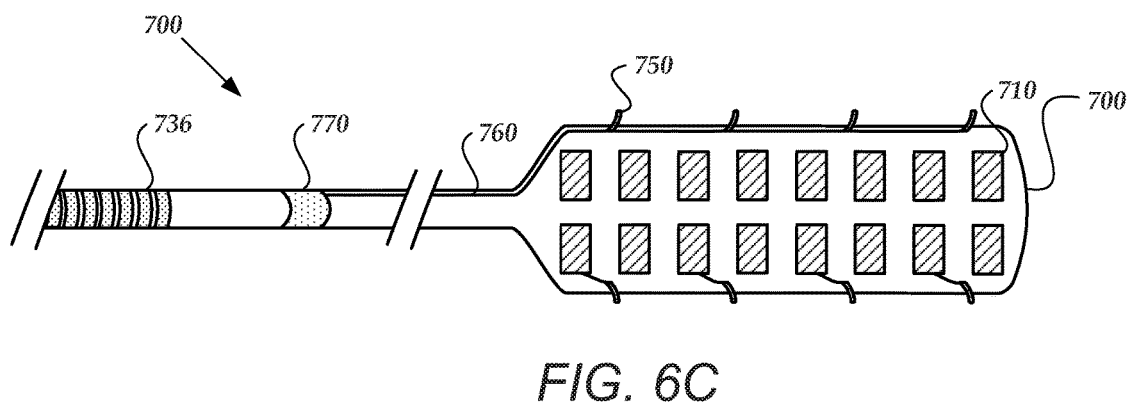
Figure 7A:
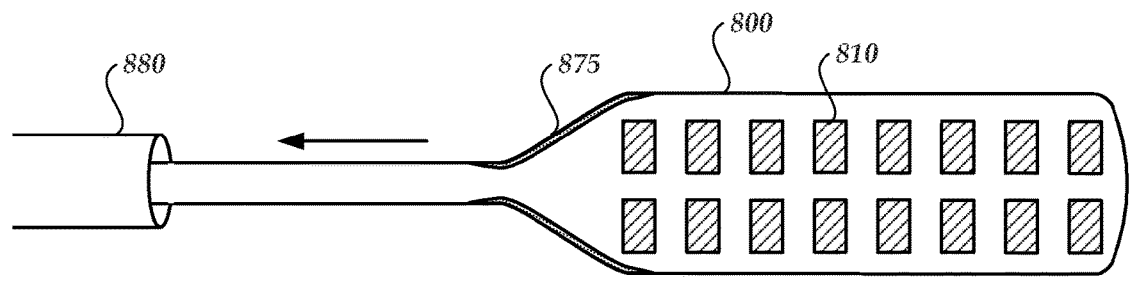
Figure 7B:
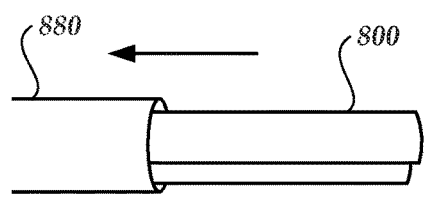
Figure 8:
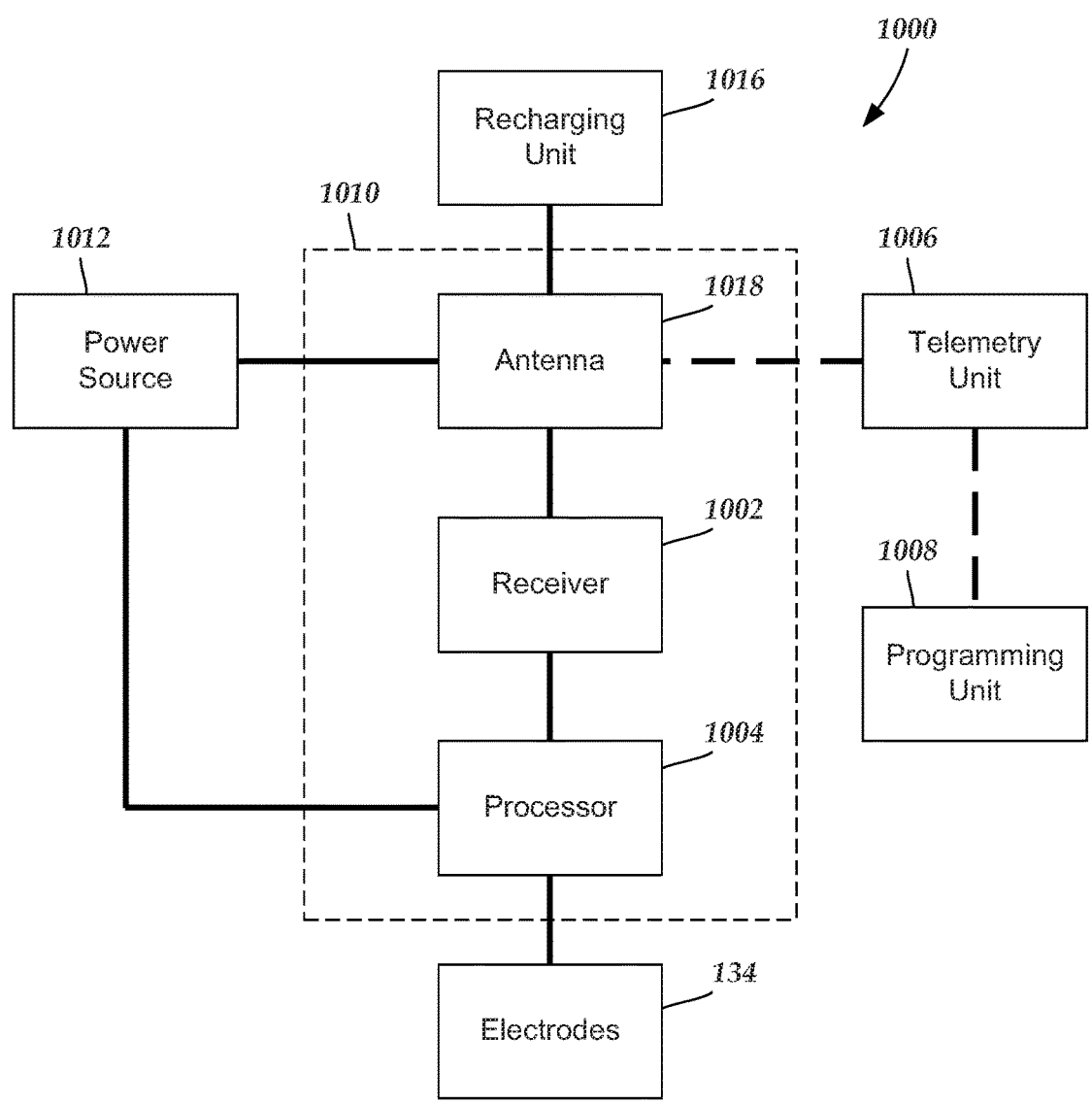

2B, the connector assembly configured and arranged to receive the lead extension of FIG. 2B, according to the invention;

FIG. 3A is a schematic cross-sectional view of one embodiment of a paddle body of a lead within bonding material, according to the invention;

FIG. 3B is a schematic cross-sectional view the paddle body of the lead of FIG. 3A during deployment, according to the invention;

FIG. 3C is a schematic cross-sectional view the paddle body of the lead of FIG. 3A after deployment, according to the invention;

FIG. 4A is a schematic cross-sectional view of one embodiment of a paddle body of a lead having a fastener, according to the invention;

FIG. 4B is a schematic top view the paddle body of the lead of FIG. 4A, according to the invention;

FIG. 4C is a schematic cross-sectional view the paddle body of the lead of FIG. 4A during deployment, according to the invention;

FIG. 4D is a schematic top view the paddle body of the lead of FIG. 4A during deployment, according to the invention;

FIG. 4E is a schematic cross-sectional view the paddle body of the lead of FIG. 4A after deployment, according to the invention;

FIG. 4F is a schematic top view the paddle body of the lead of FIG. 4A after deployment, according to the invention;

FIG. 5A is a schematic cross-sectional view of one embodiment of a paddle body of a lead having a current-sensitive binder, according to the invention;

FIG. 5B is a schematic cross-sectional view the paddle body of the lead of FIG. 5A during deployment, according to the invention;

FIG. 5C is a schematic cross-sectional view the paddle body of the lead of FIG. 5A after deployment, according to the invention;

FIG. 6A is a schematic perspective view of one embodiment of a lead having current-degradable fasteners, according to the invention;

FIG. 6B is a schematic perspective view of another embodiment of a lead having current-degradable fasteners, according to the invention;

FIG. 6C is a schematic perspective view of a third embodiment of a lead having current-degradable fasteners, according to the invention;

FIG. 7A is a schematic perspective view of one embodiment of a lead having an explant support and an explant tool before explant, according to the invention;

FIG. 7B is a schematic perspective view of the lead and explant tool of FIG. 7A during explant, according to the invention; and FIG. 8 is a schematic perspective overview of one embodiment of components of an electrical stimulation system, including an electronic subassembly disposed within a control module, according to the invention.

DETAILED DESCRIPTION

The present invention is directed to the area of devices and methods for stimulation of tissue using an array of electrode contacts, as well as methods of making and using the devices. In addition, the present invention is directed to the area of devices and methods for stimulation of tissue using a percutaneously deliverable paddle lead.

The paddle leads described herein may be percutaneously implantable. This may obviate the need for performing an invasive procedure such as a laminotomy or laminectomy for implantation of the paddle lead. Suitable implantable electrical stimulation systems include, but are not limited to, an electrode lead ("lead") with one or more electrode contacts disposed on a distal end of the lead and one or more terminals disposed on one or more proximal ends of the lead. Examples of electrical stimulation systems with leads are found in, for example, U.S. Pat. Nos. 6,181,969; 6,516,227; 6,609,029; 6,609,032; and 6,741,892; 7,244,150; 7,672,734 7,761,165; 7,949,395; 7,974,706; and U.S. Patent Applications Publication Nos. 2005/0165465, 2007/0150036; 2007/0219595; and 2008/0071320, all of which are incorporated by reference.

Figure 1:
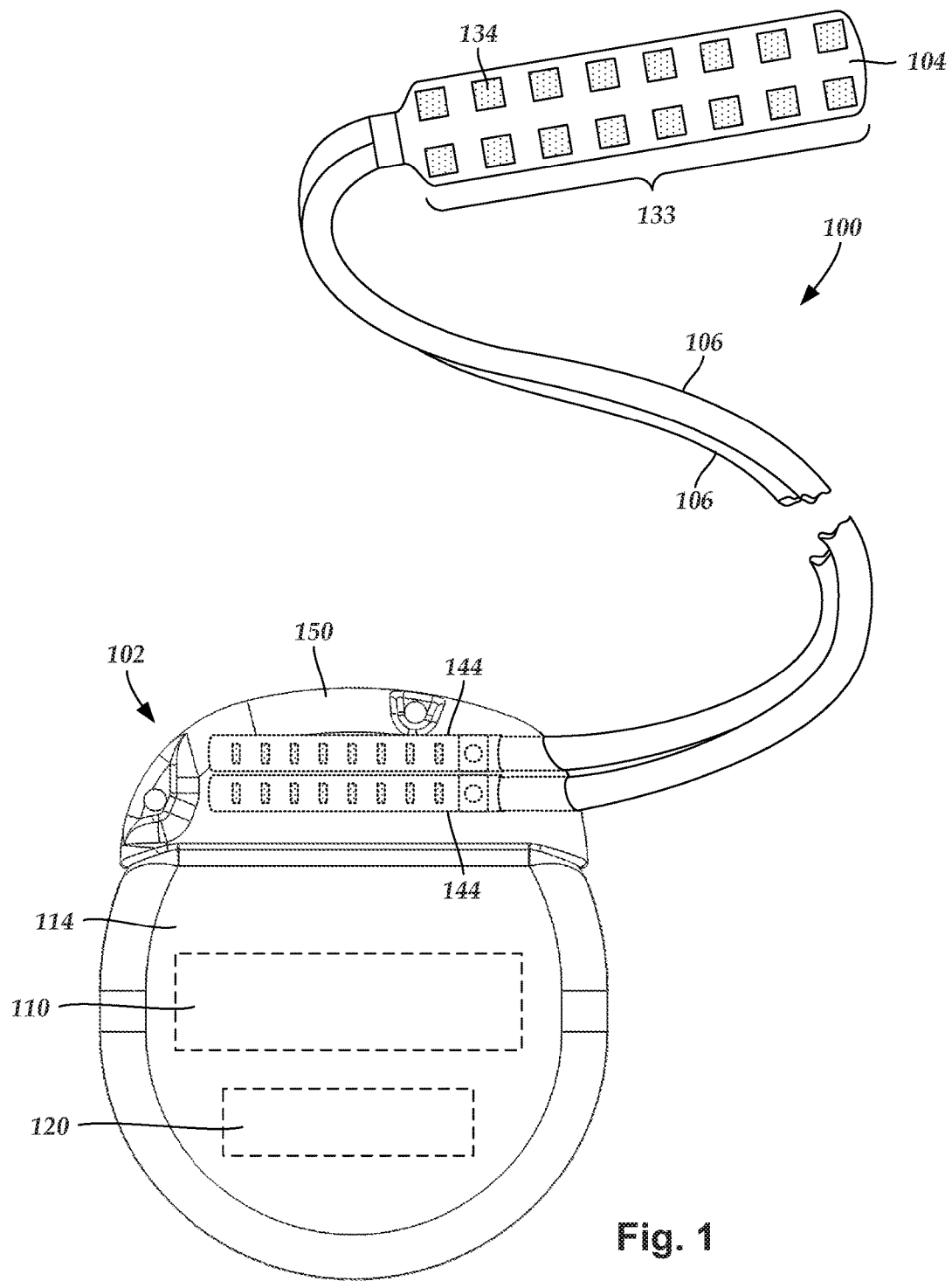
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes a plurality of electrode contacts 134 that form an array of electrode contacts 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 216 in FIG. 2A). The connector contacts are coupled to the electronic subassembly 110 and the terminals are coupled to the electrode contacts 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 224 (see FIG. 2B) can be disposed between the one or more lead bodies 106 and the control module 102 to extend the distance between the one or more lead bodies 106 and the control module 102.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrode contacts 134 can be formed using any conductive, biocompatible material. Examples of suitable materials include metals, alloys, conductive polymers, conductive carbon, and the like, as well as combinations thereof. In at least some embodiments, one or more of the electrode contacts 134 are formed from one or more of: platinum, platinum iridium, palladium, palladium rhodium, titanium, or titanium nitride.

The number of electrode contacts 134 in the array of electrode contacts 133 may vary. For example, there can be four, five, six, seven, eight, nine, ten, eleven, twelve, thirteen, fourteen, fifteen, sixteen, or more electrode contacts 134. As will be recognized, other numbers of electrode contacts 134 may also be used. In FIG. 1, sixteen electrode contacts 134 are shown. The electrode contacts 134 can be formed in any suitable shape including, for example, round, oval, triangular, rectangular, pentagonal, hexagonal, heptagonal, octagonal, or the like.

The electrode contacts of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrode contacts and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 210 in FIG. 2A) are typically disposed at the proximal end of the one or more lead bodies 106 for connection to corresponding conductive contacts (e.g., 216 in FIG. 2A) in connector assemblies disposed on, for example, the control module 102 (or to other devices, such as conductive contacts on a lead extension, an operating room cable, a lead splitter, a lead adaptor, or the like). Conductive wires (not shown) extend from the terminals to the electrode contacts 134. Typically, one or more electrode contacts 134 are electrically coupled to a terminal (e.g., 210 in FIG. 2A). In some embodiments, each terminal (e.g., 210 in FIG. 2A) is only coupled to one electrode contact 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

FIG. 2A is a schematic side view of one embodiment of the two lead bodies 106 shown in FIG. 1 configured and arranged for coupling with the control module 102. A plurality of connector assemblies 144 are disposed in the control module 102. In at least some embodiments, the control module 102 includes two, three, four, or more connector assemblies 144. Typically, the number of connector assemblies 144 disposed in the control module 102 is equal to the number of lead bodies 106 of the lead. For example, in FIG. 2A, the two lead bodies 106 shown in FIG. 1 are shown configured and arranged for insertion into two connector assemblies 144 disposed on the control module 102.

The connector assemblies 144 each include a connector housing 214 and a plurality of connector contacts 316 disposed therein. Typically, the connector housing 214 defines a port (not shown) that provides access to the plurality of connector contacts 216. In at least some embodiments, the connector assemblies 144 further include retaining elements 218 configured and arranged to fasten the corresponding lead bodies 206 to the connector assemblies 144 when the lead bodies 106 are inserted into the connector assemblies 144 to prevent undesired detachment of the lead bodies 106 from the connector assemblies 144. For example, the retaining elements 218 may include apertures through which fasteners (e.g., set screws, pins, or the like) may be inserted and secured against an inserted lead body (or lead extension).

In FIG. 2A, the plurality of connector assemblies 144 are disposed in the header 150. In at least some embodiments, the header 150 defines one or more ports 204 into which a proximal end 206 of the one or more lead bodies 106 with terminals 210 can be inserted, as shown by directional arrows 212, in order to gain access to the connector contacts 216 disposed in the connector assemblies 144.

When the lead bodies 106 are inserted into the ports 204, the connector contacts 216 can be aligned with the terminals 210 disposed on the lead bodies 106 to electrically couple the control module 102 to the electrode contacts (134 of FIG. 1) disposed at a distal end of the lead bodies 106. Examples of connector assemblies in control modules are found in, for example, U.S. Pat. No. 7,244,150 and U.S. Patent Application Publication No. 2008/0071320 A1, which are incorporated by reference.

In some instances, the electrical stimulation system may include one or more lead extensions. FIG. 2B is a schematic side view of one embodiment of a proximal end of a single lead body 106' configured and arranged to couple with a lead extension 224 that is coupled with the control module 102'. In FIG. 2B, a lead extension connector assembly 222 is disposed at a distal end 226 of the lead extension 224. The lead extension connector assembly 222 includes a contact housing 228. The contact housing 228 defines at least one port 230 into which a proximal end 206 of the lead body 106' with terminals 210 can be inserted, as shown by directional arrow 238. The lead extension connector assembly 222 also includes a plurality of connector contacts 240. When the lead body 106' is inserted into the port 230, the connector contacts 240 disposed in the contact housing 228 can be aligned with the terminals 210 on the lead body 106 to electrically couple the lead extension 224 to electrode contacts (not shown) disposed on the lead body 106'.

The proximal end of a lead extension can be similarly configured and arranged as a proximal end of a lead body, such as one of the lead bodies 106, or the lead body 106'. The lead extension 224 may include a plurality of conductive wires (not shown) that electrically couple the connector contacts 240 to terminals at the proximal end 248 of the lead extension 224. The conductive wires disposed in the lead extension 224 can be electrically coupled to a plurality of terminals (not shown) disposed on the proximal end 248 of the lead extension 224.

FIG. 2C is a schematic side view of one embodiment of the lead extension 224 configured and arranged for coupling with the control module 102'. The control module 102' includes a single connector assembly 144. Alternately, the control module 102' may receive the lead body 106' directly. It will be understood that the control modules 102 and 102' can both receive either lead bodies or lead extensions. It will also be understood that the electrical stimulation system 100 can include a plurality of lead extensions 224. For example, each of the lead bodies 106 shown in FIGS. 1 and 2A can, alternatively, be coupled to a different lead extension 224 which, in turn, are each coupled to different ports of a two-port control module, such as the control module 102 of FIGS. 1 and 2A.

Degradable binding material can be used to bind together portions of the paddle body of a paddle lead so that the paddle lead can be implanted percutaneously (e.g., through a needle, cannula, introducer or the like.) The paddle body takes on a compacted form when bound. In the compacted form, the paddle body may be folded, rolled, coiled, compressed, or otherwise deformed from its normal paddle-like form in order to permit percutaneous implantation. During or soon after implantation (for example, within one minute or within five minutes or within 10 minutes or within 30 minutes or within 1 hour or within 12 hours or within 1 day) the degradable binding material releases the paddle body allowing it deform into its normal paddle-like form.

FIG. 3A is a cross-sectional view of one embodiment of a portion of a paddle body 400 that has been folded to fit within a bonding material 450 that encapsulates the paddle body and fits within a delivery needle 460 or the like. The percutaneously implantable paddle body 400 may be formed of a flexible biocompatible, non-conductive material such as, for example, silicone, polyurethane, combinations thereof, and the like. The paddle body 400 includes electrode contacts 410 that will be used for stimulating body tissue.

The percutaneously implantable paddle body 400 is flexible and elastic so that it can be folded, rolled or otherwise compressed into a shape suitable for implantation via, for example, a percutaneous needle, cannula, or the like (not shown). The percutaneously implantable paddle body 400 is capable of changing shape after implantation. For example, the paddle body 400 may be formed of, or include, shape memory materials (e.g. nitinol) which can change shape in response to exposure to a change in temperature. Alternatively or additionally, the paddle body 400 includes a flexible material that can be rolled, coiled or bent but returns to a planar or flat surface at body temperature or a flexible material that springs back to a flat, planar shape (or any other desired paddle-like shape) when released.

The bonding material 450 can be any suitable biocompatible material that sufficiently degrades (e.g., dissolves, is bioabsorbed, disperses, or releases the paddle body) or is otherwise sufficiently removed during, or soon after (for example, within one minute or within five minutes or within 10 minutes or within 30 minutes or within 1 hour or within 12 hours or within 1 day), implantation to allow deployment of the paddle body. For example, the bonding material 450 may be a material that degrades (e.g., dissolves, is bioabsorbed, disperse, or releases the paddle body) in the presence of heat or an aqueous environment. As one example, the bonding material 450 is a sugar that dissolves in an aqueous environment. As another example, the bonding material 450 can be a material that degrades (e.g., dissolves, is bioabsorbed, disperse, or releases the paddle body) in the presence of a second agent (e.g. enzyme, solvent, protein, other biomolecule, or the like) which could be found at the implantation site or introduced into the space around the paddle body via, for example, an injection, the implantation needle or cannula, a fluid channel within the lead, an IV drip, or oral administration. Examples of suitable bonding materials, include, but are not limited to, polyglycolic acid (e.g., Biovek™), polylactic acid, polydioxanone, caprolactone, and cyanoacrylate.

In some embodiments, the bonding material 450 fully or partially encapsulates encompasses, or encases the paddle body 400 or a portion of the paddle body. In other embodiments, the bonding material 450 partially surrounds the paddle body 400 so as to maintain the paddle body as a folded shape during implantation of the paddle body. As an example, the bonding material may form a shell or cylinder around the paddle body or a portion of the paddle body or the bonding material may encapsulate one or more cross-sectional regions of the paddle body. For example, the bonding material 450 may be in the shape of rings that are disposed around the circumference of the paddle body 400. In some embodiments, one, two, three, four or five bonding rings may be disposed around the circumference of the paddle body 400. It will be understood that the shape and size of the bonding material 450 may vary.

After implantation, the bonding material 450 is at least partially degraded (e.g., dissolved, bioabsorbed, dispersed, or has released the paddle body) or is otherwise removed to allow the paddle body 400 to deploy into a paddle shape. FIG. 3B illustrates a portion of the paddle body 400 of FIG. 3B after implantation and as the bonding material is being degraded or otherwise removed. As seen in FIG. 3B, the bonding material 450 is degraded or otherwise removed so that the paddle body 400 is no longer constrained within the encapsulating bonding material 450. After degradation or removal of the bonding material 450, the bends of paddle body 400 begin to straighten so that the paddle body 400 begins to form a pre-defined planar shape (or another desired paddle-like shape).

FIG. 3C illustrates the portion of the paddle body 400 of FIG. 3A after deployment. As seen in FIG. 3C, the deployment of paddle body 400 is complete, with the paddle body forming a substantially planar surface similar to that of conventional paddle-type leads. After deployment of the paddle body 400, the stimulating electrode contacts 410 disposed on a surface of the paddle body 400 are ready for stimulating body tissue. In some embodiments, the deployed paddle body 400 may be rotated or repositioned after implantation to provide effective therapy.

FIG. 4A is a cross-sectional view of another embodiment of a paddle body 500 having fasteners 550 that degrade (e.g., dissolve, are bioabsorbed, disperses, or release the paddle body) or are otherwise removed during or shortly after implantation to release the paddle body. FIG. 4B is a side view the portion of the paddle body 500 of FIG. 4A. As seen in FIGS. 4A and 4B, the paddle body 500 is wrapped circumferentially with the electrode contacts 510 on the inside of the wrapped paddle body 500. It will be understood that the paddle body 500 may be wrapped in other shapes before implantation. For example, the paddle body 500 may be folded over, or wrapped around, the longitudinal or lateral centerline for implantation. The wrapped shape of the paddle body 500 before implantation is maintained using one or more fasteners 550 disposed along the length of the paddle body 500. The fastener 550 may be, for example, a clasp, rivet, tie, pin, or clip useful for coupling two portions of the paddle body 500. Any number of fasteners may be disposed along the length of the paddle body 500. In some embodiments, one, two, three, four, five, six, seven, eight, ten, twelve or fourteen fasteners are disposed along the length of the paddle body.

The fasteners are formed of a material that sufficiently degrades (e.g., dissolves, is bioabsorbed, disperses, or releases the paddle body) or is otherwise sufficiently removed during, or soon after, implantation, to allow deployment of the paddle body. Materials such as those described above with respect to the bonding material 450 are generally suitable for the fasteners. For example, the fasteners 550 may be formed of a material that degrades (e.g., dissolves, is bioabsorbed, disperses, or releases the paddle body) in the presence of heat or an aqueous environment. In some embodiments, the fasteners 550 are formed of a sugar. In some embodiments, the fasteners 550 are formed of a material that degrades (e.g., dissolves, is bioabsorbed, disperses, or releases the paddle body) in the presence of a second agent which could be introduced into the epidural space. In some embodiments, only partially degrading or otherwise removing the fasteners during or after implantation allows the paddle body to deploy (e.g., unfold.) It will be understood that, in some embodiments, remnants of the fasteners may remain attached to the paddle body for a period of time or even indefinitely.

FIG. 4C is a cross-sectional view the portion of the paddle body of FIG. 4A during deployment. FIG. 4D is a side view the portion of the paddle body of FIG. 4C during deployment. As seen in FIGS. 4C and 4D, at least partial degradation, dissolution, or removal of fasteners 550 initiates the beginning of deployment of the paddle body 500. In some embodiments, the paddle body 500 is formed of a shape memory material that reverts to a substantially flat or planar shape after removal of the fasteners 550.

FIG. 4E is a cross-sectional view the portion of the paddle body of FIG. 4A after deployment. FIG. 4F is a side view the portion of the paddle body of FIG. 4A after deployment. As seen in these figures, the deployed paddle body 500 may be similar in shape and size to conventional paddle bodies, yet is easier and less expensive to implant.

In another embodiment, one or more binding elements may be disengaged or degraded using electrical current. FIG. 5A is a cross-sectional view of one embodiment of a portion of a paddle body 600 with one or more electrode contacts 610 and one or more current-degradable fasteners 650. As seen in FIG. 5A, the paddle body 600 is wrapped similar to the percutaneously implanted paddle leads of the previous embodiments. The sides of the paddle body 600 are held together using one or more current-degradable fasteners 650. The current-degradable fasteners 650 may have any suitable shape or size. In some embodiments, the current-degradable fasteners 650 are formed of a material or combination of materials that degrades, weakens, or melts when at least a threshold electrical current is applied. For example, the fastener can be made using two different metals where at least one of the metals is thin, has relatively high impedance, or has a low melting temperature (or any combination of these features) such that application of current will degrade, weaken, or melt the metal or joint between the metals. As another example, the fastener may be made of a combination of materials that experience electrolytic detachment when current is applied, such as, for example, platinum and stainless steel or tungsten and stainless steel.

The threshold electrical current may depend on the type of material or materials used and the physical arrangement of the fastener. With the current-degradable fastener(s) 650 holding the sides of the paddle body 600 together, the wrapped paddle body 600 may be percutaneously implanted into body tissue at a suitable position. Current is then applied to the fastener(s) 650 so that the fastener(s) break and the sides of the paddle body 600 are released, allowing the paddle body to assume its flat, planar shape (or any other suitable paddle-like shape).

FIG. 5B is a schematic cross-sectional view the portion of the lead of FIG. 5A during deployment. As seen in FIG. 5B, a current may be introduced to the current-sensitive binder 650 to break the binder after implantation. As seen in FIG. 5B, breaking of the current-sensitive binder 650 allows the lead 600 to straighten into the eventual shape of a conventional percutaneous lead 600. FIG. 5C is a schematic cross-sectional view the portion of the lead of FIG. 5A after full deployment.

Illustrating an example of a lead with current-degradable fasteners, FIG. 6A is a schematic perspective view of one embodiment of a paddle body 700 of a lead 705 having current-degradable fasteners 750. As seen in FIG. 6A, the paddle body 700 is in the deployed position and includes electrode contacts 710 disposed on a face of the lead 700. The paddle body 700 also includes the remnants of current-degradable fasteners 750 on the edges of the paddle body 700. These remnants are provided for illustrative purposes, but it will be understood that, at least in some embodiments, the current-degradable fasteners may be completely removed from the paddle body upon deployment.

As seen in FIG. 6A, the percutaneously implantable lead 705 can include deployment contacts 770 disposed on the lead 705. The deployment contacts 770 may be formed of any suitable material including metals, alloys, conductive polymers, conductive carbon, and the like, as well as combinations thereof. For example, the deployment contacts 770 may be ring contacts similar to those used in percutaneous leads. Alternatively, other contact arrangements can be used.

Conductors 760 couple the deployment contacts 770 to the current-degradable fasteners 750. The current degradable fasteners 750 can be arranged in parallel, as illustrated in FIG. 6A, or in series or any combination thereof. With the current degradable fasteners 750 disengaged, the lead 705 resembles a conventional paddle-type lead.

FIG. 6B illustrates another embodiment in which the lead 700 has only a single deployment contact 770. The return electrode (not shown) for current flowing through the deployment contact 770, conductor 760, and current-degradable fasteners 750 is remote from the lead 705. For example, the return electrode may be provided on the patient's skin or implanted elsewhere in the patient's body.

FIG. 6C illustrates yet another embodiment in which the electrode contacts 710 of the paddle body 700 and associated terminals 736 act as the return electrode(s) for the current-degradable fasteners 750. Alternatively, the terminals 736 and electrode contacts 710 may act as the active electrode contacts with the conductor 760 and deployment contact 770 acting as the return electrode. In yet another embodiment, the current-degradable fasteners 750 may be electrically coupled to at least two of the electrode contacts 710 of the paddle body 700 so that flow of current between the electrode contacts causes degradation of the fasteners and deployment of the paddle body.

Some embodiments include structures on the proximal end of the paddle body that facilitate percutaneous explant of the lead. Such structures can be incorporated into any paddle body that is capable of folding to fit within a percutaneous explant tool (e.g., a needle) and can be used, if desired, with any of the other embodiments discussed above. FIG. 7A illustrates a paddle body 800 with electrode contacts 810 and explant structures 875 disposed at the proximal end of the paddle body 800. The explant structure 875 facilitate folding of the lead when encountering an explant tool 880, as illustrated in FIG. 7B. The explant structure illustrated in FIG. 7A is a tapered end that provides a leading edge when the paddle is retracted into a needle. The paddle is formed such that this leading edge initiates the "roll-up" of the paddle. Examples of paddle formations that lend themselves to this "roll-up" include, but are not limited to, a flexible ridge down the center of the paddle, a slightly "C" shaped profile, a very thin paddle, or any combination thereof. As another example, a draw-string type mechanism could be employed that allows a user to make adjustments at the proximal end of the lead (e.g. the activation of a draw string coupled to the paddle) to initiate pull back and roll-up of the paddle at the distal end of the lead.

FIG. 8 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In at least one embodiment, electrical current is emitted by the electrode contacts 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrode contacts can be used to provide stimulation, if desired. In some embodiments, the processor 1004 may select which electrode(s) are cathodes and which electrode (s) are anodes. In some embodiments, the processor 1004 may be used to identify which electrode contacts provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrode contacts, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A percutaneously implantable paddle lead, comprising:
   an elongated lead body having a proximal portion and a distal portion;
   a plurality of terminals disposed on the proximal portion of the lead body;

a flexible paddle body coupled to the distal portion of the lead body, wherein the paddle body is compacted into a compacted form that is percutaneously implantable;

a plurality of electrodes disposed in the paddle body and electrically coupled to the terminals on the proximal portion of the lead body; and a plurality of current-degradable fasteners in contact with the paddle body and holding the paddle body in its compacted form prior to, and during, insertion into a percutaneous implantation tool, wherein the current-degradable fasteners are configured and arranged to release the paddle body upon application of at least a threshold current to allow the paddle body to deploy into its paddle-like form.

2. The paddle lead of claim 1, wherein the paddle body is rolled around a longitudinal centerline of the paddle lead.

3. The paddle lead of claim 1, wherein each of the current-degradable fasteners is at least one clasp, rivet, tie, pin, or clip.

4. The paddle lead of claim 1, further comprising at least one deployment contact disposed on the lead body and at least one conductor coupling the at least one deployment contact to the current-degradable fasteners.

5. The paddle lead of claim 1, wherein each of the current-degradable fasteners is electrically coupled to at least one of the plurality of electrodes.

6. The paddle lead of claim 1, wherein the paddle body has a first longitudinal edge and a second longitudinal edge opposite the first longitudinal edge and the current-degradable fasteners attach the first longitudinal edge to the second longitudinal edge.

7. The paddle lead of claim 1, wherein the paddle body in the compacted form is a cylinder.

8. The paddle lead of claim 7, wherein the electrodes of the paddle body in the compacted form are disposed on an interior of the cylinder.

9. The paddle lead of claim 1, wherein each of the current-degradable fasteners comprises a metal having a low melting temperature to melt the current-degradable fastener when current is applied to the current-degradable fastener.

10. A method of percutaneously implanting an implantable paddle lead, the method comprising:

inserting at least a paddle body of the paddle lead into a percutaneous insertion tool, the paddle body is compacted into a compacted form that is percutaneously implantable, the paddle lead further comprising a degradable binding material in contact with the paddle body and holding the paddle body in its compacted form;

implanting the paddle body near tissue to be stimulated in a body of a patient; and degrading the binding material by exposing the binding material to heat, moisture, or a biomolecule in the body of the patient to release the paddle body from its compacted form and allow it to deploy to its paddle-like form, wherein the exposure causes the binding material to readily degrade and release the paddle body.

11. The method of claim 10, wherein degrading the binding material comprises exposing the binding material to the heat in the body of the patient, wherein the exposure causes the binding material to readily degrade and release the paddle body.

12. The method of claim 10, wherein degrading the binding material comprises exposing the binding material to the moisture in the body of the patient, wherein the exposure causes the binding material to readily degrade and release the paddle body.

13. The method of claim 10, wherein degrading the binding material comprises exposing the binding material to the biomolecule in the body of the patient, wherein the exposure causes the binding material to readily degrade and release the paddle body.

14. The method of claim 10, wherein the binding material forms at least one band disposed around a portion of the paddle body.

15. The method of claim 10, wherein the binding material forms at least one fastener.

16. The method of claim 15, wherein the at least one fastener is at least one clasp, rivet, tie, pin, or clip.

17. The method of claim 10, wherein the paddle body in the compacted form is a cylinder.

18. The method of claim 17, wherein the electrodes of the paddle body in the compacted form are disposed on an interior of the cylinder.

19. A method of percutaneously implanting an implantable paddle lead, the method comprising:

inserting at least a paddle body of the paddle lead into a percutaneous insertion tool, the paddle body is compacted into a compacted form that is percutaneously implantable, the paddle lead further comprising a degradable binding material in contact with the paddle body and holding the paddle body in its compacted form;

implanting the paddle body near tissue to be stimulated in a body of a patient; and degrading the binding material by applying at least a threshold current to the binding material causing the binding material to degrade and release the paddle body from its compacted form and allow it to deploy to its paddle-like form.

* * * * *